US011026750B2

(12) United States Patent
Fichtinger et al.

(10) Patent No.: US 11,026,750 B2
(45) Date of Patent: Jun. 8, 2021

(54) REAL-TIME SURGICAL NAVIGATION

(71) Applicants: Queen's University at Kingston, Kingston (CA); Kingston Health Sciences Centre, Kingston (CA)

(72) Inventors: Gabor Fichtinger, Kingston (CA); Tamas Ungi, Kingston (CA); John F. Rudan, Kingston (CA); Andras Lasso, Kingston (CA); C. Jay Engel, Kingston (CA); Gabrielle Gauvin, Kingston (CA); Caitlin Yeo, Kingston (CA)

(73) Assignees: Queen's University at Kingston, Kingston (CA); Kingston Health Sciences Centre, Kingston (CA)

( * ) Notice: Subject to any disclaimer, the term of this patent is extended or adjusted under 35 U.S.C. 154(b) by 1018 days.

(21) Appl. No.: 15/004,289

(22) Filed: Jan. 22, 2016

(65) Prior Publication Data

US 2016/0242855 A1    Aug. 25, 2016

Related U.S. Application Data

(60) Provisional application No. 62/106,983, filed on Jan. 23, 2015.

(51) Int. Cl.
*A61B 34/20* (2016.01)
*A61B 34/00* (2016.01)
(Continued)

(52) U.S. Cl.
CPC .............. *A61B 34/20* (2016.02); *A61B 5/062* (2013.01); *A61B 17/320016* (2013.01);
(Continued)

(58) Field of Classification Search
CPC ......... A61B 34/20; A61B 5/062; A61B 34/76; A61B 17/320016; A61B 2017/3413;
(Continued)

(56) References Cited

U.S. PATENT DOCUMENTS 6,016,439 A * 1/2000 Acker ...................... A61B 5/06
600/411
6,379,302 B1 * 4/2002 Kessman ............. A61B 8/0841
600/437

(Continued)

OTHER PUBLICATIONS

Krekel, N.M.A., et al., "Intraoperative ultrasound guidance for palpable breast cancer excision (COBALT trial): a multicentre, randomised controlled trial", Lancet Oncol., vol. 14, 48-54, (2013).
(Continued)

*Primary Examiner* — Malina D. Blaise
(74) *Attorney, Agent, or Firm* — Stephen J. Scribner

(57) ABSTRACT

An apparatus and method for surgical tracking comprises an imaging device that generates an image of a tissue volume; an electromagnetic (EM) sensor that creates a reference frame for EM tracking in three dimensions; at least one EM sensor adapted to be attached to the tissue to track local deformation and movement of the tissue volume; a processor that registers the image with the EM-tracked tissue volume and surgical tool in real time, and produces an output; and a feedback device that provides feedback about the location of the surgical tool relative to the tissue volume, based on the processor output. Embodiments are particularly useful in soft tissue, such as breast, where deformation before and during a procedure such as tumor resection complicate tracking of the tissue volume and a surgical tool.

21 Claims, 12 Drawing Sheets

(51) Int. Cl.
*A61N 5/10* (2006.01)
*A61B 17/32* (2006.01)
*A61B 5/06* (2006.01)
*A61B 17/00* (2006.01)
*A61B 17/34* (2006.01)

(52) U.S. Cl.
CPC ............ *A61B 34/76* (2016.02); *A61N 5/1001* (2013.01); *A61B 17/3403* (2013.01); *A61B 2017/008* (2013.01); *A61B 2017/00115* (2013.01); *A61B 2017/00292* (2013.01); *A61B 2017/3405* (2013.01); *A61B 2017/3413* (2013.01); *A61B 2034/2051* (2016.02); *A61N 5/1015* (2013.01); *A61N 5/1049* (2013.01)

(58) Field of Classification Search
CPC ...... A61B 17/3403; A61B 2017/00292; A61B 2034/2051; A61B 2017/00115; A61B 2017/008; A61B 2017/3405; A61N 5/1001; A61N 5/1015; A61N 5/1049
See application file for complete search history.

(56) References Cited

U.S. PATENT DOCUMENTS

| | | | | |
|---|---|---|---|---|
| 7,751,868 | B2* | 7/2010 | Glossop | A61B 5/06 600/407 |
| 7,840,251 | B2 | 11/2010 | Glossop | |
| 8,504,139 | B2 | 8/2013 | Jacobsen et al. | |
| 8,605,964 | B2* | 12/2013 | Fichtinger | G06T 7/33 382/128 |
| 8,948,845 | B2 | 2/2015 | Glossop et al. | |
| 8,957,812 | B1* | 2/2015 | Hill | G01S 5/0027 342/445 |
| 10,194,830 | B2* | 2/2019 | George | A61B 18/1492 |
| 10,456,595 | B2* | 10/2019 | Ribbing | A61N 5/1001 |
| 2004/0019274 | A1* | 1/2004 | Galloway, Jr. | A61B 90/36 600/425 |
| 2005/0101855 | A1* | 5/2005 | Miga | G06K 9/00214 600/407 |
| 2005/0119566 | A1* | 6/2005 | Sasso | A61B 17/3468 600/429 |
| 2008/0123927 | A1* | 5/2008 | Miga | G06F 19/00 382/131 |
| 2008/0161680 | A1* | 7/2008 | von Jako | A61B 5/06 600/424 |
| 2011/0077504 | A1* | 3/2011 | Fischer | A61B 34/30 600/411 |
| 2011/0082383 | A1* | 4/2011 | Cory | A61B 5/0536 600/547 |
| 2011/0098569 | A1* | 4/2011 | Warmath | G09B 23/285 600/443 |
| 2011/0137156 | A1* | 6/2011 | Razzaque | A61B 18/1477 600/424 |
| 2012/0330635 | A1* | 12/2012 | Miga | G06T 7/33 703/11 |
| 2013/0063434 | A1* | 3/2013 | Miga | A61B 90/36 345/420 |
| 2013/0287167 | A1* | 10/2013 | Gum | A61N 5/1049 378/20 |
| 2014/0037161 | A1* | 2/2014 | Rucker | A61B 5/0033 382/128 |
| 2014/0148808 | A1* | 5/2014 | Inkpen | G01B 7/003 606/80 |
| 2015/0142372 | A1* | 5/2015 | Singh | A61B 5/4851 702/150 |
| 2015/0157384 | A1* | 6/2015 | Hoey | A61B 18/04 600/104 |
| 2015/0287236 | A1* | 10/2015 | Winne | G06F 3/147 382/128 |
| 2015/0306423 | A1* | 10/2015 | Bharat | A61B 34/30 600/427 |
| 2016/0022146 | A1* | 1/2016 | Piron | A61B 90/39 600/411 |
| 2016/0070436 | A1* | 3/2016 | Thomas | A61B 5/055 715/771 |
| 2016/0135776 | A1* | 5/2016 | Chandler, Jr. | G01R 33/4812 600/411 |
| 2017/0014203 | A1* | 1/2017 | De Mathelin | A61B 5/055 |
| 2017/0046833 | A1* | 2/2017 | Lurie | G06T 19/20 |
| 2017/0105601 | A1* | 4/2017 | Pheiffer | A61B 1/00009 |
| 2017/0112586 | A1* | 4/2017 | Dhupar | A61B 90/13 |

OTHER PUBLICATIONS

Liberman, L., et al., "Bracketing Wires for Preopertive Breast Needle Localization", American Journal of Roentgenology, vol. 177, 565-572, (2001).
Sajid, M.S., et al., "Comparison of Radioguided Occult Lesion Localization (ROLL) and Wire Localization for Non-Palpable Breast: A Meta-Analysis", Journal of Surgical Oncology, vol. 105, 852-858, (2012).
Shah, A.P., et al., "Expanding the use of real-time electromagnetic tracking in radiation oncology", Journal of Applied Clinical Medical Physics, vol. 12, No. 4, 34-49, (2011).
Ungi, T. et al., "Spinal Needle Navigation by Tracked Ultrasound Snapshots", IEEE Transactions on Biomedical Engineering, vol. 59, No. 10, 2766-2772, (2012).
Gauvin, G., et al., "Real-time EM navigated breast conserving surgery, phantom and cadaver experiments", Seventh Image Guided Therapy Workshop, MIT, Cambridge, MA, Sep. 18, 2014.
Gauvin, G. et al., "Real-Time Electromagnetic Navigation for Breast Tumor Resection: Proof of Concept", The Hamlyn Symposium on Medical Robotics, Imperial College London, UK, Jul. 2014.
Gauvin, G. et al., "Real-Time Electromagnetic Navigation for Breast Tumor Resection: Proof of Concept", Candian Surgery Forum, Vancouver, BC, Sep. 19-20, 2014 (Abstract).
Gauvin, G. et al., "Real-Time Electromagnetic Navigation for Breast Tumor Resection: Proof of Concept", 7th Annual Research Meeting, Faculty of Health Sciences, Queen's University, Kingston, ON, Jun. 3, 2014 (Abstract).
Gauvin, G. et al., "Real-Time Electromagnetic Navigation for Breast Tumor Resection: Proof of Concept", MICCAI-IT, 2014.
Maier-Hein, L. et al., "Precision Trageting of Liver Lesions with a Needle-Based Soft Tissue Navigation System", Medical Image Computing and Computer-Assisted Intervention—MICCAI, 42-49, Springer Berlin Heidelberg (2007).

* cited by examiner

```
<DataCollection >
  <Device Id="TrackerDevice" Type="Ascension3DG"
   AcquisitionRate="50" ToolReferenceFrame="Tracker" >
    <DataSources>
      <DataSource Type="Tool" Id="Reference" PortName="0" />
      <DataSource Type="Tool" Id="Stylus" PortName="1" />
    </DataSources>
    <OutputChannels>
      <OutputChannel Id="TrackerStream" >
        <DataSource Id="Reference"/>
        <DataSource Id="Stylus"/>
      </OutputChannel>
    </OutputChannels>
  </Device>
  <Device Id="VideoDevice" Type="SonixVideo"
   AcquisitionRate="30" LocalTimeOffsetSec="0" IP="127.0.0.1" >
    <DataSources>
      <DataSource Type="Video" Id="Video" PortName="B"
        PortUsImageOrientation="UF" />
    </DataSources>
    <OutputChannels>
      <OutputChannel Id="VideoStream" VideoDataSourceId="Video" />
    </OutputChannels>
  </Device>
  <Device Id="TrackedVideoDevice" Type="VirtualMixer" >
    <InputChannels>
      <InputChannel Id="TrackerStream" />
      <InputChannel Id="VideoStream" />
    </InputChannels>
    <OutputChannels>
      <OutputChannel Id="TrackedVideoStream"/>
    </OutputChannels>
  </Device>
</DataCollection>
```

Fig. 8

REAL-TIME SURGICAL NAVIGATION

RELATED APPLICATION

This application claims the benefit of the filing date of U.S. Application No. 62/106,983, filed on Jan. 23, 2015, the contents of which are incorporated herein by reference.

FIELD

This invention is in the field of surgical navigation methods and apparatus. More specifically, this invention relates to techniques, methods, and apparatus that provide electromagnetic real-time surgical navigation.

BACKGROUND

Surgical resection procedures require precise delineation of the tissue being removed. This is particularly important in tumor resection, where precise delineation of tumor margins is critical to successful treatment. The problem is compounded in deformable soft tissue, such as the breast, which may move during setup and registration of surgical navigation equipment, as well as during the resection procedure.

Breast cancer is ideally treated by breast-conserving surgery (e.g., lumpectomy) during its early stage. FIG. 1A shows the incision 14, which avoids the need to remove skin, the tumor 10, and the breast tissue removed as defined by a margin 12. The balance between adequate surgical margins and cosmesis is a current challenge. Precise delineation of the breast tumor margins is difficult because lesion margins are commonly not physically well defined and, as noted above, breast tissue moves and deforms during the procedure. FIG. 1B shows a negative margin 15 (left) in which the tumor 16 is completely surrounded by non-tumor tissue 18. A positive margin 17 is shown in FIG. 1B (right), wherein the tumor 16 is not completely surrounded by non-tumor tissue 18. With current strategies, the positive margin rate at initial excision may be as high as 47%. The presence of a positive margin is linked with high local recurrence rate despite adjuvant radiotherapy, and therefore leads to the patient requiring another surgery to remove the remaining cancer tissue.

The current standard procedure to localize the tumor before surgery is wire-localization under radio logic guidance. On the day of the surgery, a radiologist places a needle in the tumor using real time ultrasound or X-ray imaging, depending on which indicates the tumor location. A localization wire is placed in the tumor through this needle. The wire marks the tumor location for the surgeon, who cuts around the wire at a radius that is deemed to be safe, but not too wide in order to spare healthy tissue. The problem with this method is that the surgeon does not know how the exact tumor margins relate to the localization wire. It only gives an approximate guide on what part of the tissue should be excised. This problem is exacerbated when the tumor is not palpable and/or not visible.

The wire-localization method only identifies the lesion at a single point, with limited ability to guide a three-dimensional resection. It also does not account for tissue deformation. Bracketing the lesion with multiple wires does not improve the rates of margin positivity. In addition, the wires are placed several hours pre-operatively and can often migrate prior to surgery.

Other tumor marking strategies include intraoperative ultrasonography, cryoprobe assisted localization, oncoplastic surgery, or radiographic markers. Radio-guided occult lesion localization, where a radiotracer solution is injected adjacent to the lesion and detected intra-operatively with a gamma ray detection counter, is also a relatively new option. All these methods suffer from one or more of the following problems: alter the surgical workflow, prohibitively expensive, technically difficult to implement, and fail to define the actual tumor margin.

SUMMARY

One aspect of the invention provides a surgical tracking method, comprising: generating an image of a tissue volume; using electromagnetic (EM) tracking to three-dimensionally delineate and track the tissue volume and a surgical tool; registering the image with the EM-tracked tissue volume and surgical tool in real time; and using the registering to provide feedback about the location of the surgical tool relative to the tissue volume.

One embodiment of the surgical navigation method comprises: disposing one or more localization devices in a tissue volume; generating images of the tissue volume; three-dimensionally delineating a portion of the tissue volume from data points in the images of the tissue volume; using electromagnetic (EM) tracking and the one or more localization devices to three-dimensionally register the delineated portion of the tissue volume with a surgical tool in real time; and providing feedback about the location of the surgical tool relative to the delineated portion of the tissue volume.

One embodiment comprises displaying and dynamically updating the three-dimensional delineation of the portion of the tissue volume as data points from the images are added or removed.

Generating the image may comprise using ultrasound, computed tomography, magnetic resonance imaging, or projection imaging (e.g., X-ray), or a combination thereof. EM tracking may comprise creating a global frame of reference for EM tracking; using at least one EM sensor attached to the tissue to track local deformation and movement of the tissue volume; and using an EM sensor to track movement of the surgical tool.

Creating the global frame of reference for EM tracking may comprise using an EM sensor attached to the patient. Using at least one EM sensor track local deformation and movement of the tissue volume may comprise using an EM sensor attached to each of one or more wire-localization needles.

In one embodiment, at least one wire-localization needle comprises two or more hooks that anchor the needle in the tissue.

Embodiments may be applied to a surgical procedure, a tissue resection procedure, optionally wherein the tissue volume comprises a tumor, or a radiation therapy procedure such as brachytherapy. In one embodiment the resection procedure is a lumpectomy in breast tissue.

Another aspect of the invention provides an apparatus for surgical tracking, comprising: an ultrasound device that generates an image of a tissue volume; an electromagnetic (EM) sensor that creates a reference frame for EM tracking in three dimensions; at least one EM sensor adapted to be attached to the tissue to track local deformation and movement of the tissue volume; a processor that registers the image with the EM-tracked tissue volume and surgical tool in real time, and produces an output; and a feedback device that provides feedback about the location of the surgical tool relative to the tissue volume, based on the processor output.

Another aspect of the invention provides an apparatus for surgical tracking, comprising: an electromagnetic (EM) sensor that creates a reference frame for EM tracking in three dimensions; at least one EM sensor adapted to be attached to the tissue to track local deformation and movement of the tissue volume; a processor that receives an image from an imaging device and registers the image with the EM-tracked tissue volume and surgical tool in real time, and produces an output; and a feedback device that provides feedback about the location of the surgical tool relative to the tissue volume, based on the processor output.

In one embodiment the apparatus comprises: an electromagnetic (EM) device that creates a reference frame for EM tracking in three dimensions; one or more localization devices adapted to be attached to tissue and to provide EM tracking of local deformation and movement of a tissue volume; an EM sensor adapted to be attached to a surgical tool; a processor that receives images of the tissue volume from an imaging device, generates a three-dimensional delineation of a portion of the tissue volume from data points in the images of the tissue volume; and three-dimensionally registers the delineated portion of the tissue volume with the surgical tool in real time; and an output device.

The EM sensor that creates a reference frame may comprise an EM sensor attached to the patient. The at least one EM sensor adapted to be attached to the tissue may comprise at least one wire-localization needle. The at least one wire-localization needle may comprise two or more hooks that anchor the needle in the tissue.

Another aspect of the invention provides programmed media for use with a processor, comprising: code stored on non-transitory storage media compatible with the processor, the code containing instructions to direct the processor to: receive image data and generate an image of a tissue volume; receive EM tracking data and use the EM tracking data to three-dimensionally delineate and track the tissue volume and a surgical tool; register the image with the EM-tracked tissue volume and surgical tool in real time; and provide feedback about the location of the surgical tool relative to the tissue volume.

In one embodiment the programmed media comprises: code stored on non-transitory storage media compatible with the processor, the code containing instructions to direct the processor to: receive images of a tissue volume and generate a three-dimensional delineation of a portion of the tissue volume from data points in the images; receive EM tracking data and use the EM tracking data to three-dimensionally register the delineated portion of the tissue volume with an EM-tracked surgical tool in real time; and produce an output comprising images of the EM-tracked surgical tool registered in the delineated portion of the tissue volume in real time.

In some embodiments, the feedback may comprise one or more of visual, tactile, and auditory feedback. The surgical tool may comprise a cutting tool, a cautery tool, a radiotherapy tool (e.g., a catheter, a linear accelerator, a needle, a device to deliver external beam radiation therapy, etc.), or any other tool such as a tissue ablator.

In some embodiments, imaging may include using ultrasound, computed tomography, magnetic resonance imaging, or projection imaging (e.g., X-ray), or a combination thereof. As described herein, EM tracking of the tumor allows for fusion of all such imaging modalities in the same frame of reference.

BRIEF DESCRIPTION OF THE DRAWINGS

For a greater understanding of the invention, and to show more clearly how it may be carried into effect, embodiments will be described, by way of example, with reference to the accompanying drawings, wherein;

FIG. 8 is an example of a SlicerIGT configuration file.

DETAILED DESCRIPTION OF EMBODIMENTS

Embodiments described herein use real-time electromagnetic (EM) tracking to three-dimensionally delineate and track tumor volume and a surgical tool, allowing a surgeon to navigate around the tumor and improve the precision of a tumor resection or other procedure. EM-based navigation technology as described herein may be adapted for a variety of surgical procedures and minimally invasive interventions. However, the embodiments are particularly suitable for procedures in soft or deformable tissue, such as breast. For demonstrative purposes, embodiments relating to breast tumor resection will be described. It will be readily understood by those of ordinary skill in the art that the invention is not limited thereto, as embodiments may be applied to any organ, tissue, or structure, and corresponding procedure. Embodiments may also be applied to other procedures, such as, for example, radiation therapy interventions such as brachytherapy. Example 2, below, describes a brachytherapy procedure wherein an embodiment is adapted to guiding the delivery of breast radiation therapy. Thus, the tracked surgical tool is not limited to a cutting or cautery tool, as in the case of a surgical (e.g., resection) procedure; rather, the tool type is determined by the procedure. Accordingly, as used herein, the term "tool" or "surgical tool" is intended to refer to any tracked instrument, tool, or device that may be used or adapted for use with the apparatus and methods described herein for surgical and radiation therapy interventions.

According to the embodiments, mobile and deformable target tissue is delineated and tracked with one or more real-time position sensors, where the sensors allow estimation of the pose of the moving/deforming target volume. If the target tissue is reasonably rigid, then one position sensor may be sufficient. The tracked position sensors comprise, for example, localization needles, or other suitable hardware that may be placed and anchored in tissue for localization of the target tissue, such as pins, clips, and the like. A localization needle may comprise multiple hooks or prongs to anchor it to the tissue, to improve tracking. In procedures where the target tissue is palpable and hence reasonably rigid, only one tracked localization needle may be required; whereas in other cases involving non-palpable tissue, multiple localization needles may be used.

Figure 4:
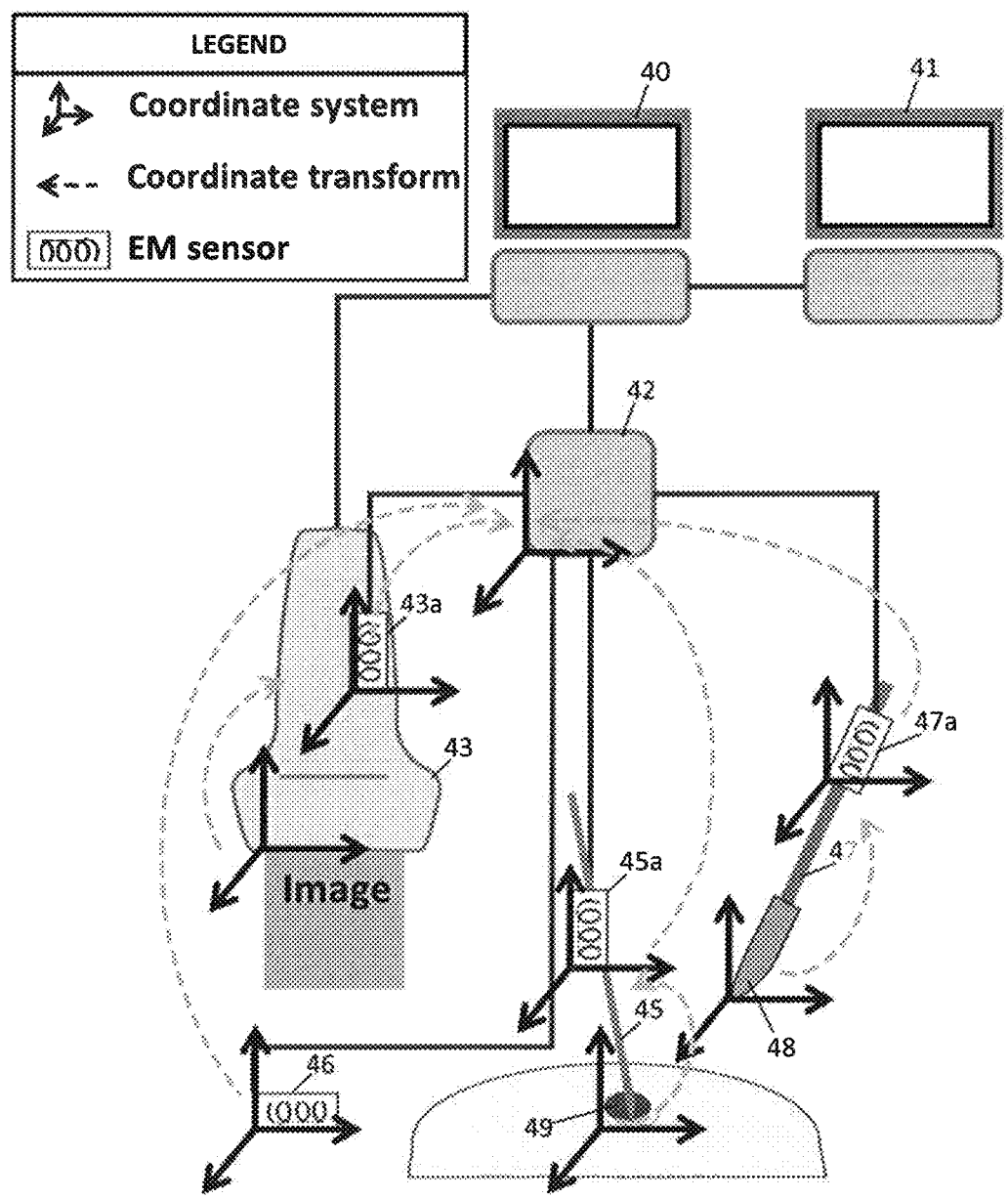
FIG. 4 is a schematic diagram of an EM navigation system, according to one embodiment.
Figure 5A:
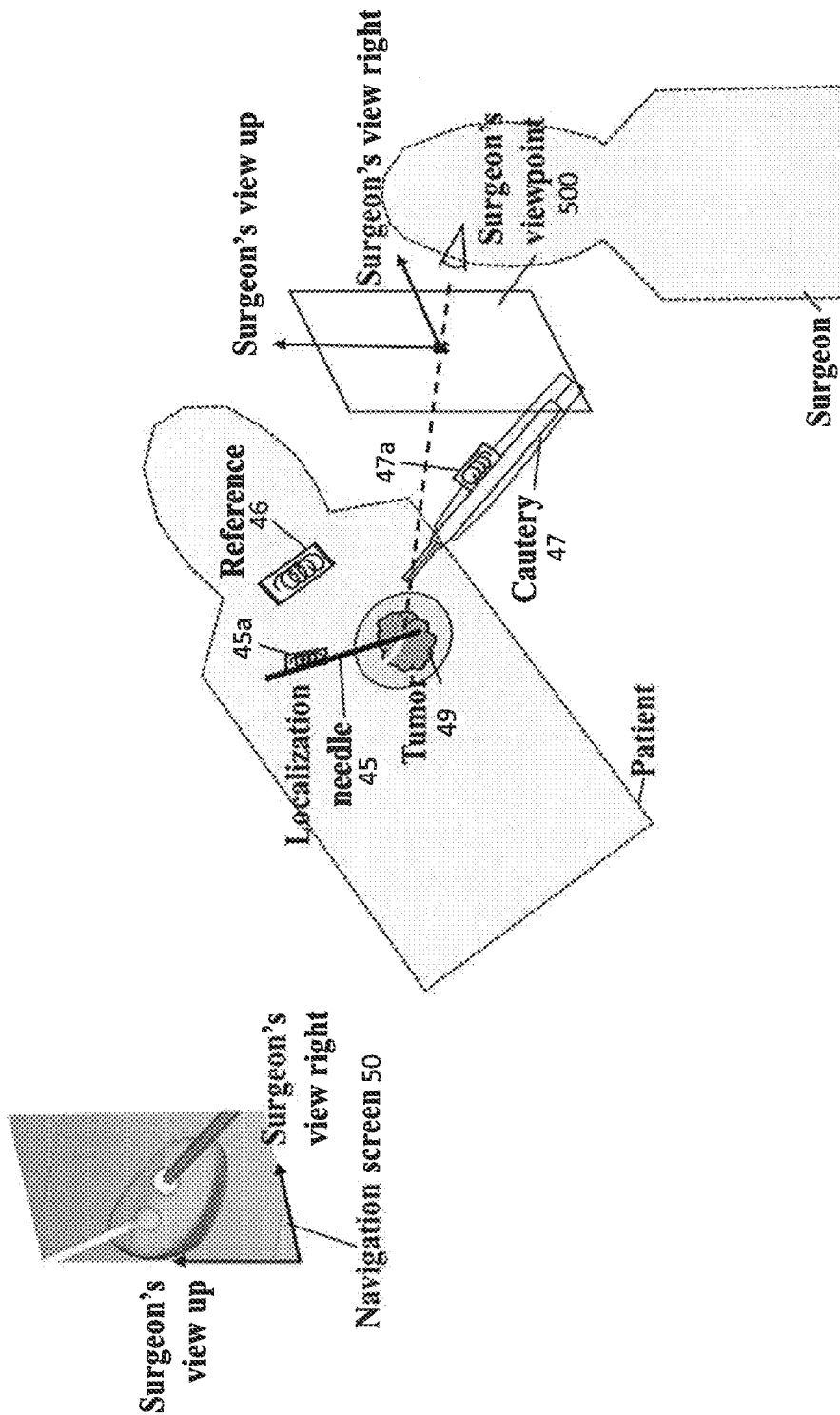
FIG. 5A is a schematic diagram showing a navigation screen and patient's anatomy and surgical tools aligned with the actual surgeon's viewpoint, according to one embodiment.
Figure 6:
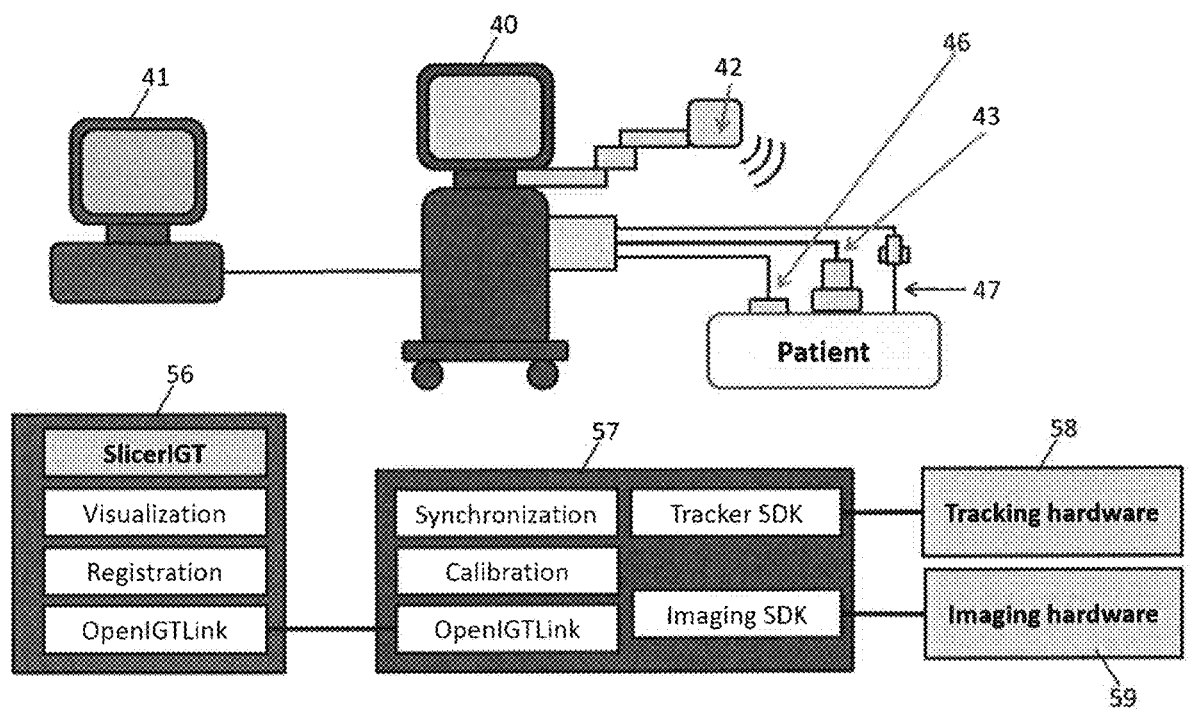
FIG. 6 is a diagram of a surgical navigation system, according to one embodiment.

Embodiments include a data processing system that controls the navigation system, such as that shown in FIGS. 4, 5A, and 6, for real-time EM tracking and facilitates the three-dimensional delineation and tracking of tumor volume for resection or radiotherapy procedures. The data processing system, in conjunction with a graphical user interface (GUI), may include functions such as receiving input (image data such as ultrasound data, commands from a user of the system, etc.), analyzing data, and displaying results and/or images on a display of the system.

The data processing system may be a client and/or server in a client/server system. For example, the data processing system may be a server system or a personal computer (PC) or tablet-based system. The data processing system may include an input device, a central processing unit (CPU), memory, display device, and interface device. The input device may include a keyboard, a mouse, a trackball, a touch sensitive surface or screen, or a similar device. The display may include a computer screen, television screen, display screen, terminal device, a touch sensitive display surface or screen, or a hardcopy producing output device such as a printer or plotter. The memory may include a variety of storage devices including internal memory and external mass storage typically arranged in a hierarchy of storage as understood by those skilled in the art. For example, the memory may include databases, random access memory (RAM), read-only memory (ROM), flash memory, and/or disk devices. The interface device may include one or more network connections. The data processing system may be adapted for communicating with other data processing systems over a network via the interface device. For example, the interface device may include an interface to a network such as the Internet and/or another wired or wireless network (e.g., a wireless local area network (WLAN), a cellular telephone network, etc.). Thus, the data processing system may be linked to other data processing systems by the network. The CPU may include or be operatively coupled to dedicated coprocessors, memory devices, or other hardware modules. The CPU is operatively coupled to the memory which stores an operating system for general management of the system. The CPU is operatively coupled to the input device for receiving user commands or queries and for displaying the results of these commands or queries to the user on the display. Commands and queries may also be received via the interface device and results may be transmitted via the interface device. The data processing system may include a database system (or storage) for storing data and programming information. The database system may include a database management system and a database and may be stored in the memory of the data processing system. In general, the data processing system has stored therein data representing sequences of instructions which when executed cause certain steps of the method described herein to be performed. For example, the instructions may be associated with components 56 and 57 of FIG. 6, components 60, 62, and 64 of FIG. 7, and the configuration file of the embodiment of FIG. 8. Of course, the data processing system may contain additional software and hardware, a description of which is not necessary for understanding the invention.

Figure 1A:
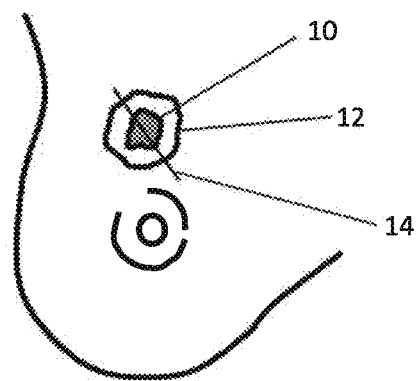
FIG. 1A is a diagram showing a lumpectomy plan in breast tissue.
Figure 1B:
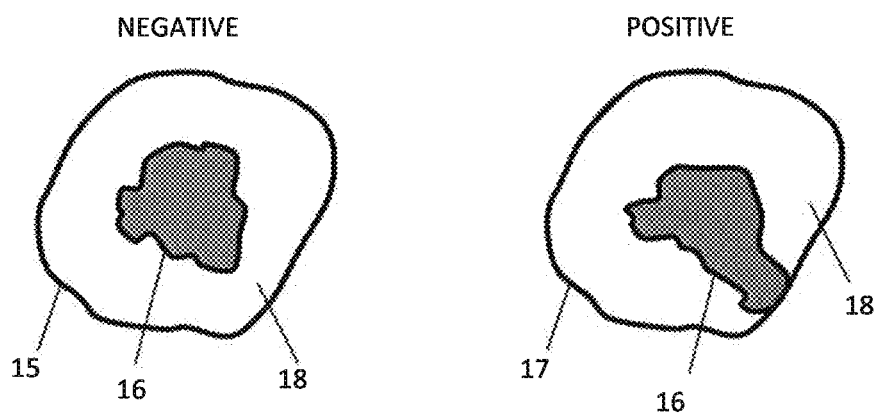
FIG. 1B is a diagram showing negative and positive margins of tumor excision.
Figure 2:
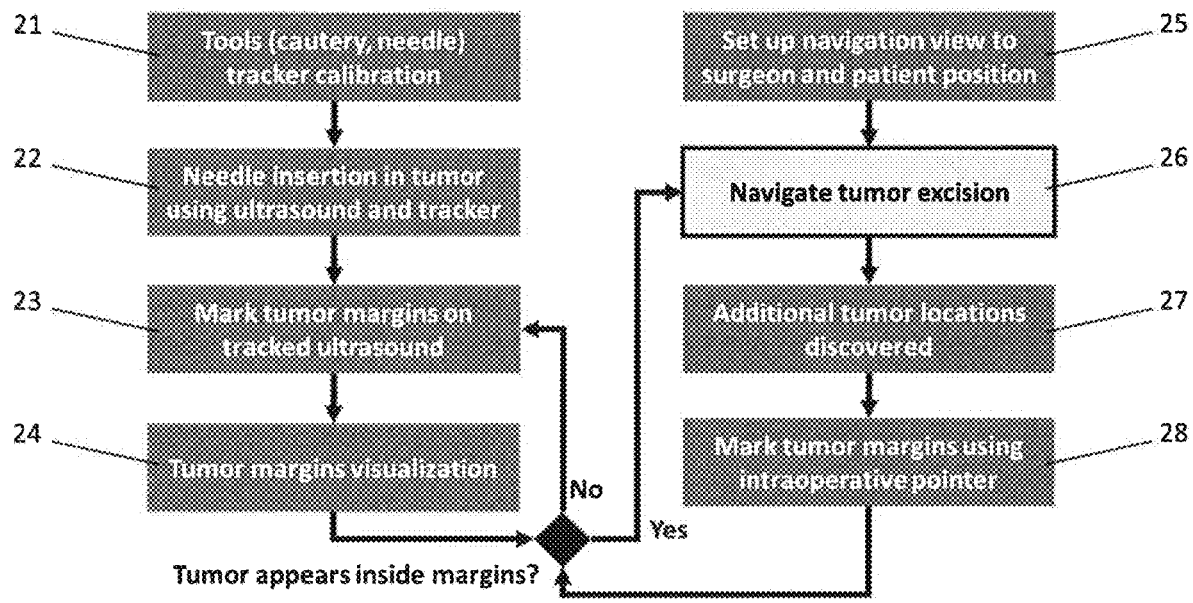
FIG. 2 is a generalized workflow diagram of real-time surgical navigation according to one embodiment.
Figure 3:
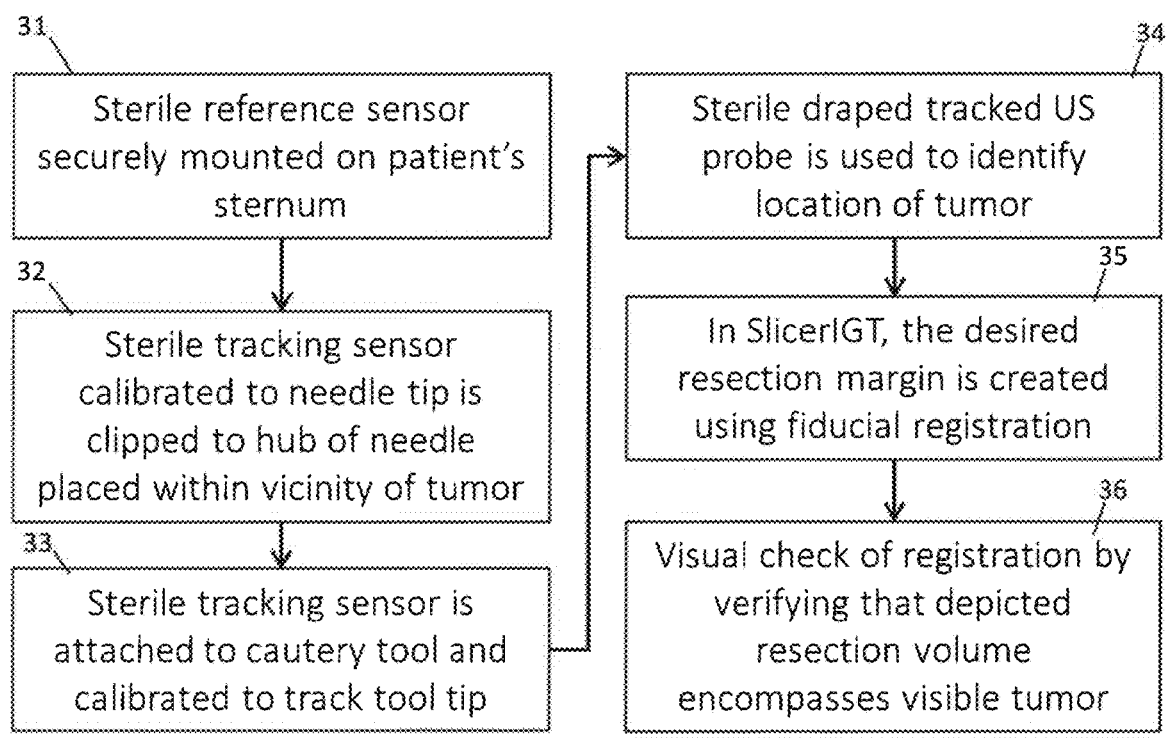
FIG. 3 is a workflow diagram of a sensor placement and registration process, according to one embodiment.

Thus, the data processing system includes computer executable programmed instructions for directing the system to implement the embodiments of the invention. Executing instructions may include the system prompting the user for input at various steps, some of which are shown in the embodiments of FIGS. 2 and 3. In one embodiment the programmed instructions may be embodied in one or more hardware modules or software modules resident in the memory of the data processing system or elsewhere. In one embodiment the programmed instructions may be embodied on a non-transitory computer readable storage medium or product (e.g., a compact disk (CD), etc.) which may be used for transporting the programmed instructions to the memory of the data processing system and/or for executing the programmed instructions. In one embodiment the programmed instructions may be embedded in a computer-readable signal or signal-bearing medium (or product) that is uploaded to a network by a vendor or supplier of the programmed instructions, and this signal or signal-bearing medium may be downloaded through an interface to the data processing system from the network by end users or potential buyers.

Figure 11:
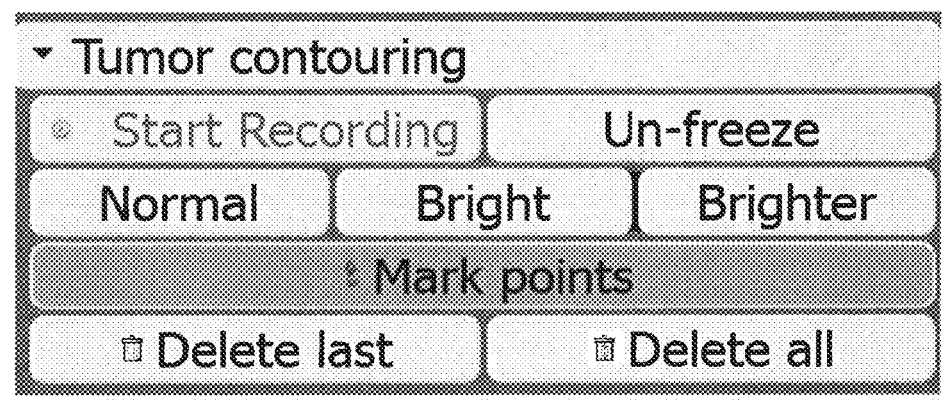
FIG. 11 is a screen capture of a graphical user interface for controlling the segmentation process during entering of tumor margins.

A user may interact with the data processing system and its hardware and software modules using a GUI. The GUI may be used for controlling, monitoring, managing, and accessing the data processing system and test system, as shown in the embodiment of FIG. 11. GUIs are supported by common operating systems and provide a display format which enables a user to choose commands, execute application programs, manage computer files, and perform other functions by selecting pictorial representations known as icons, or items from a menu through use of an input device such as a mouse or touch screen. In general, a GUI is used to convey information to and receive commands from users and generally includes a variety of GUI objects or controls, including icons, toolbars, drop-down menus, text, dialog boxes, buttons, and the like. A user typically interacts with a GUI presented on a display by using an input device (e.g., a mouse or touchscreen) to position a pointer or cursor over an object (e.g., an icon) and by "clicking" on the object. Typically, a GUI based system presents application, system status, and other information to the user in one or more "windows" appearing on the display. A window is a more or less rectangular area within the display in which a user may view an application or a document. Such a window may be open, closed, displayed full screen, reduced to an icon, increased or reduced in size, or moved to different areas of the display. Multiple windows may be displayed simultaneously, such as: windows included within other windows, windows overlapping other windows, or windows tiled within the display area.

Real-time surgical navigation embodiments may be implemented according to the generalized workflow shown in the embodiments of FIGS. 2 and 3 and the schematics in the embodiments of FIGS. 4 and 6. According to these embodiments, an EM tracked ultrasound (US) probe is used to identify and register the tumor location and delineate the desired resection volume intra-operatively. An EM sensor is attached to the surgical instrument (e.g., a cautery device) to allow real-time visualization of the surgical instrument relative to the planned resection volume. A wire-localization needle is placed within the tumor, creating a locally rigid region immediately surrounding the tumor. Several needles may be used to achieve more accurate localization. The needle is anchored in place using the deployment of two or more hooks at the needle tip. The EM sensor may be attached to the needle hub. The needle tip position is computed with respect to the needle EM sensor. As the needle and tissue in the vicinity of the tumor is manipulated during surgery, the EM transmitter is able to continuously track the location of the tumor based on its relationship to the needle. The desired surgical excision margins are defined through points placed on tracked US images of the tumor using a human-computer interface. A convex 3-dimensional shape is computed from margin points. This shape models the boundaries of the tumor tissue to be surgically removed. The computed tumor model is shown in the surgical navigation screen.

Figure 9:
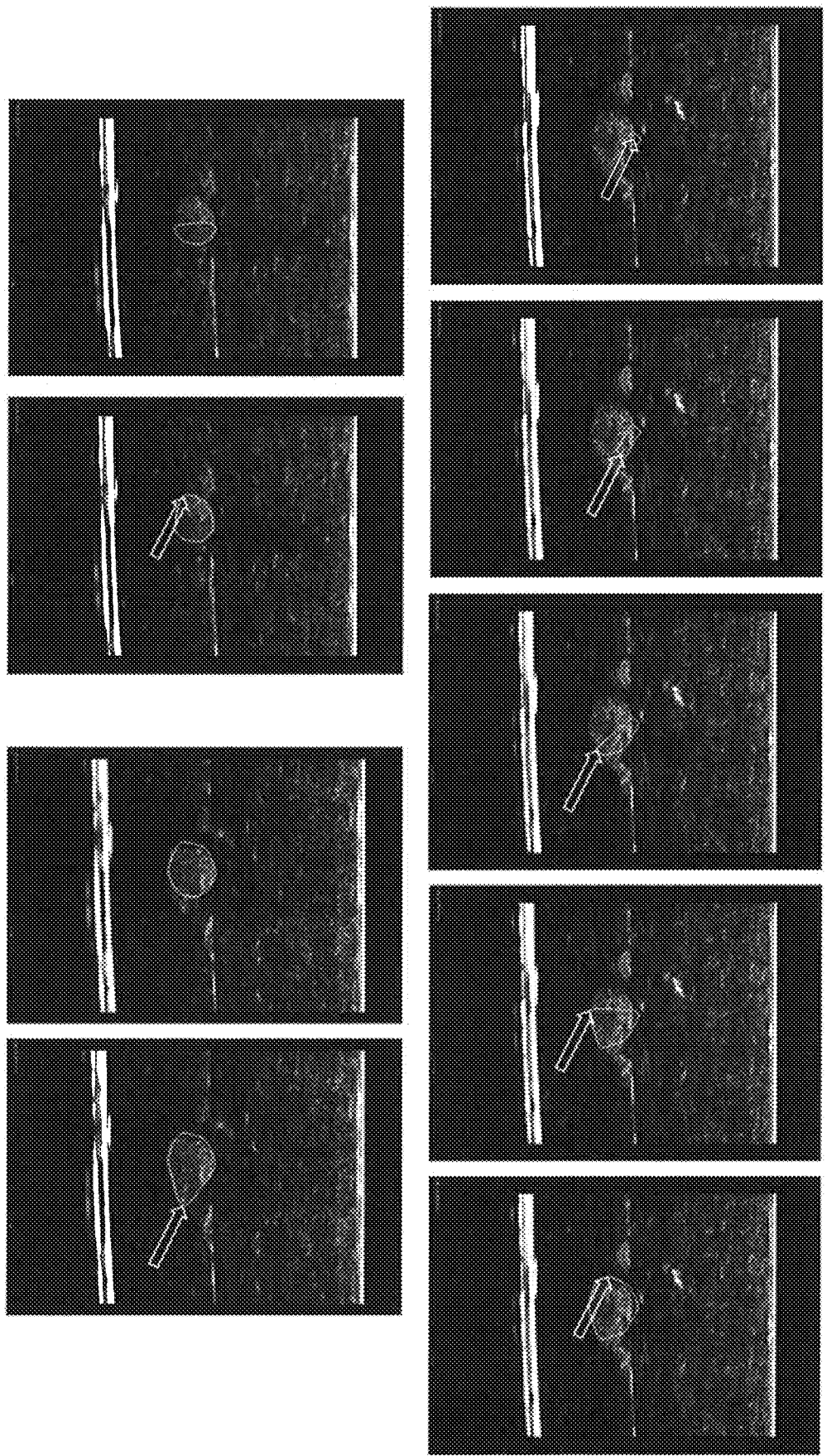
FIG. 9 shows an example of tumor segmentation by defining points in tracked ultrasound images, where the arrow tip indicates a touched position on the image.
Figure 10:
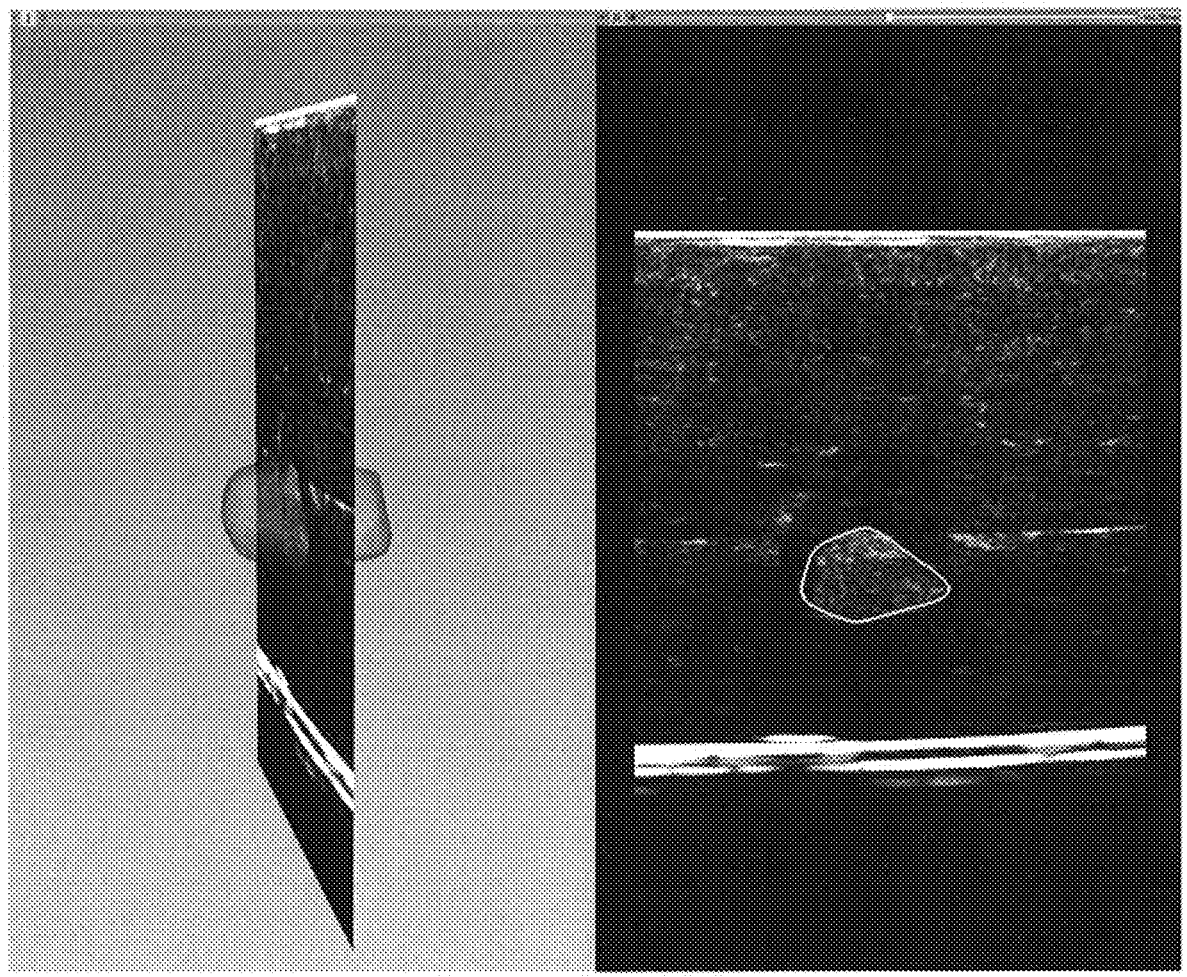
FIG. 10 is a screen capture showing a 2D intersection contour of a shape (e.g., a tumor) as displayed (right panel), and the corresponding shape generated in 3D (left panel).

Embodiments will now be described in greater detail. Referring to FIG. 2, step 21 involves the calibration of surgical tools such as the cutting tool (e.g., cautery tool) and wire-localization needle(s). In step 22, the needle(s) are inserted into the tumor using ultrasound imaging and EM tracking. At step 23, the clinician delineates the tumor margin. This may be done quickly, and may require using only one hand, which may be advantageous in certain situations. The tumor shape in 3D is delineated by identifying tumor boundary points on 2D ultrasound slices. This may be done, e.g., by tapping each point on the images displayed on a touch-screen of a computer or tablet. The 3D shape is constructed from these points. As points are added or removed, the 3D shape is updated and substantially immediately displayed. An example showing a sequence of images is shown in FIG. 9, where the arrow tip indicates a touched position. The 3D shape is generated so that it encloses the points that the clinician defined, while minimizing volume (such that the points typically lie at the object boundary surface), and with a boundary surface as smooth as possible. FIG. 10 is a screen capture showing a 2D intersection contour of a shape (e.g., a tumor) as displayed (right panel), and the corresponding shape generated in 3D (left panel). If the clinician is not satisfied with the result, more points may be added. If a point is defined incorrectly, the clinician can click the "Delete" button, which removes the most recently added point. After the clinician has defined tumor points in a number of image planes (e.g., 2-3), a sweep over the entire tumor may be used to ensure the tumor is fully enclosed in the generated shape. Additional points may be added until the entire tumor is covered and may be viewed (step 24).

A screen capture from the display of an input device (e.g., a touchscreen) of a GUI for controlling the segmentation process is shown in the example of FIG. 11. In one embodiment, by clicking the "Delete last" button repeatedly the most recently added points can be removed in order, eventually until all points are removed, if desired. If the "Delete all" button is pressed then all points are removed at once. In one embodiment points may also be removed based on where they are. For example, the user may switch to a "delete" mode wherein all points around a position the user touches are deleted. A "correction" mode may also be provided, wherein when a point is added at the position the user touches, all nearby points are deleted.

FIG. 3 shows a typical sensor placement and registration workflow, including reference sensor placement 31, calibration of the tracking sensor to the needle tip at 32 and to the surgical tool tip at 33, US localization of the tumor at 34, creation of the resection margin at 35, and visual verification of the resection volume at 36.

Step 25 of FIG. 2 and step 31 of FIG. 3 relate to setting up the navigation system, and embodiments of the overall navigation system are shown in FIGS. 4 and 6. In these embodiments, an ultrasound machine 40 (e.g., SonixGPS Tablet, Ultrasonix, Vancouver, CA) was used with its built-in EM tracker 42 offering multiple sensor ports. The US scanner 43 with FM sensor 43a and tracker 42 broadcast data through the open-source PLUS toolkit (www.plustoolkit.org) to the SlicerIGT navigation software (www.SlicerIGT.org; see Ungi T, et al., Spinal needle navigation by tracked ultrasound snapshots, IEEE Trans. Biomed, Eng. 59(10)2766-72, 2012) running on the navigation computer 41, providing real-time registration and visualization of the resection volume and tool 47 with EM sensor 47a (i.e., tool tip 48) position with respect to the reference sensor 46. An EM sensor 45a was attached to the localization needle 45 using a flexible clip, and is shown inserted into the tumor 49. Depending on the configuration of the parts, the sensor may be inserted into the clip's body and this assembly placed into a sterile plastic bag. The clip may be fixed to the needle base in such a way that rotation around the needle is prevented (e.g., the clip may engage the needle's hub). Depending on the hooked needle's construction, the localization needle may slightly rotate around the deployed wire hook. In this case, a small amount of glue (e.g., standard sterile cyanoacrylate tissue glue) may be applied into the needle hub to prevent rotation.

Setting up a conventional navigation system includes setting up the displays to show the patient in an orientation that matches the orientation from the surgeon's point of view. This may include manually defining one or more of image flip flags, rotation angles, and the approximate position of the patient, surgeon, and equipment. However, manual operations are time-consuming, may require assistance, and include the possibility of introducing errors.

Embodiments overcome the disadvantages of manual setup by automatically setting up views, and allowing precise tuning by the surgeon using only existing equipment (i.e., using equipment already present in the operating room, as standard equipment for any procedure), with a sterile interface. Moreover, implementing the embodiments does not modify equipment in any way that would impede the surgeon's ability to perform a procedure. In one embodiment, standard anatomical views are aligned with patient axes, therefore only image flip flags have to be specified (e.g., how to orient left/right, superior/inferior, anterior/posterior axes). In one embodiment, all flags are determined from a reference EM sensor 46 that is attached to the patient (see FIGS. 4, 5A, and 6), aligned with anatomical axes. The reference sensor may be attached (e.g., taped) to the skin of the patient in a convenient location, aligned with patient left/right, superior/inferior axes.

The reference EM sensor 46 is attached externally to the patient to create a global frame of reference, and an EM sensor 45a is attached to the wire-localization needle 45 to account for local deformation and movement of the tissue. The reference device attached to the patient's anatomy may be, for example, as described in U.S. Patent Application Publication No. 2014/0276001 A1. The reference device is placed on the patient's chest or other convenient location to provide anatomical reference to the navigation system. This allows the navigation display to be presented in a perspective that corresponds to an operator's perspective. A virtual camera perspective may be adjusted by switching the surgical (e.g., cautery) tool to a "camera controller mode". This allows the operators to set the optimal virtual camera positions on the 3-dimensional virtual reality display of the navigation system.

In one embodiment, shown in FIG. 5A, the surgeon's view on the navigation screen 50 shows anatomy and tools aligned with the actual surgeon's viewpoint (shown schematically at 500). For example, if the surgeon moves a tool to left/right/up/down, then the tool moves left/right/up/down on the screen too. The view is specified by the view "normal" direction (direction of the line connecting surgeon's viewpoint and the point be looks at; view "up" direction; and focal point (position that is shown in the center of the view). These can all be determined fully automatically from the positions of tracked tools (e.g., reference sensor 46, localization needle 45, and cautery/cutting tool 47). Optionally, the orientation may be determined manually by moving the tracked tool. Table 1 summarizes different scenarios.

TABLE 1

Example of automatic and manual orientation scenarios

| | Automatic | Manual |
|---|---|---|
| View "normal" direction | computed as the line connecting tracked tooltip position and the tracked localization needle tip position | tracked tool long axis |
| View "up" direction | vertical up direction, determined from the reference sensor's orientation | tracked tool "up" direction (e.g., towards the buttons on a cautery tool) |
| Focal point | tracked localization needle tip position | direction that the tracked tool long axis points |

In one embodiment, a fully automatic mode is provided wherein the surgeon holds the tool in front of him/herself, and orientation is computed automatically. In another embodiment, a manual view orientation mode is provided wherein the surgeon moves the tool to specify view normal direction, and view up and focal point are determined automatically. Only the tool tip position is used. In another embodiment, a fully manual mode is provided wherein the surgeon moves and orients the tracked tool to define view directions and focal point manually. The tool orientation and tip position are used.

Figure 5B:
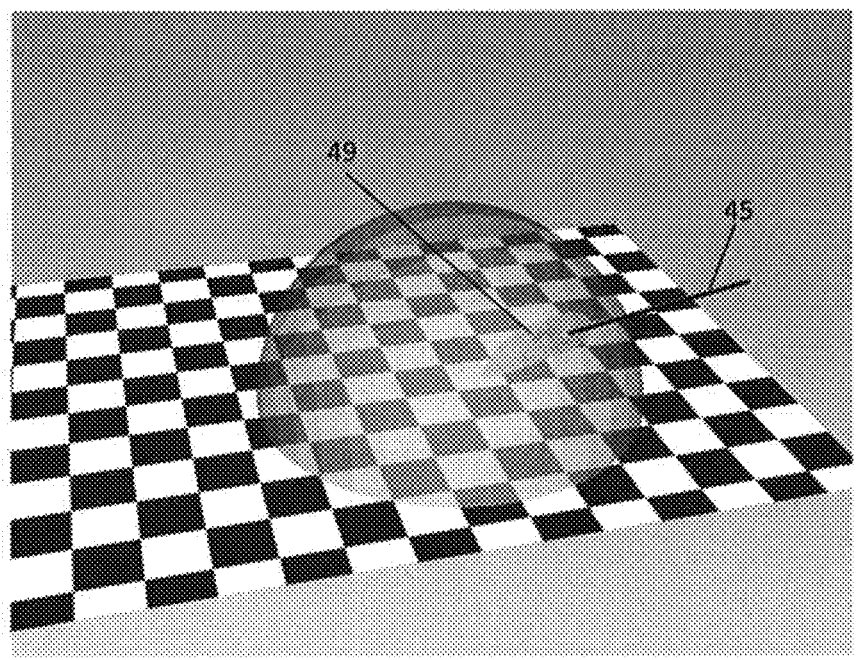
FIGS. 5B and 5C are examples of images showing approximate visualization of the breast surface and the operating table, used to augment the navigation view.
Figure 5C:
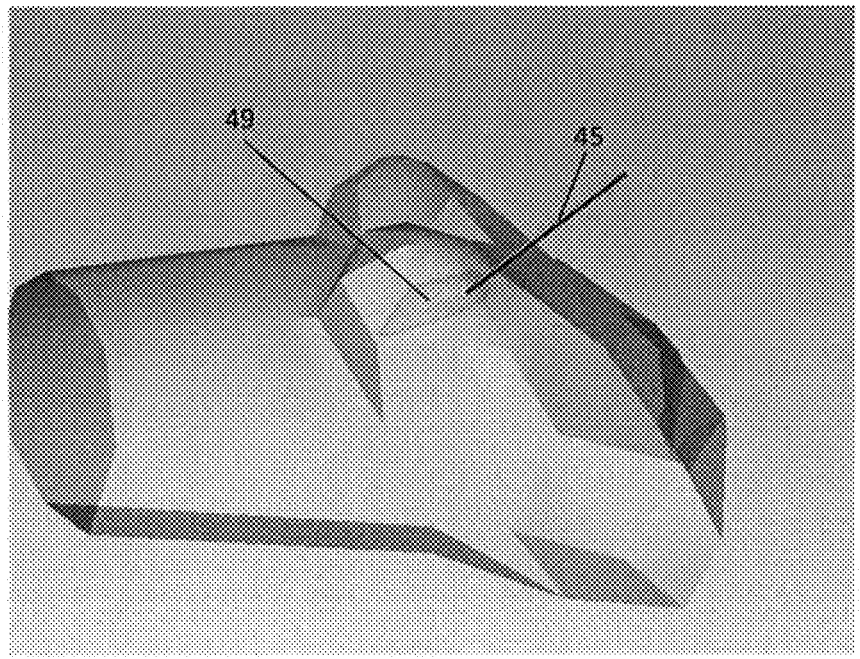

To help the surgeon in determining directions, sizes, and distances, the navigation view may be augmented with an approximate visualization of the breast surface and the operating table, as shown in FIGS. 5B and 5C. In various embodiments, the breast surface/shape may be approximated using one or more of the following ways:

From the surface that the ultrasound transducer touches while scanning (presence of skin contact is determined automatically from the image content).
By fitting a shape such as a half spheroid, determined by fitting a surface on points and curves defined by touching the breast skin surface or moving very closely to the skin surface.
By applying 3D imaging methods (e.g., using depth cameras, surface scanners, etc.).

An image including a generic table and full patient model may be generated as, e.g., fixed size and shape, or adjusted based on inputs such as table width, patient size, etc., and displayed based on position and orientation of the reference sensor.

During navigation of the surgical tool (step 26 of FIG. 2) several feedback options may be provided to the surgeon. Proximity of the tool to the tumor may trigger one or more of audio feedback, colour feedback on the navigation display, additional visual feedback (LED light) on the cautery tool, and tactile feedback (e.g., in the handle of the tool). In one embodiment, at least one of the visual feedback signals is always in the field of view of the surgeon.

Figure 7:
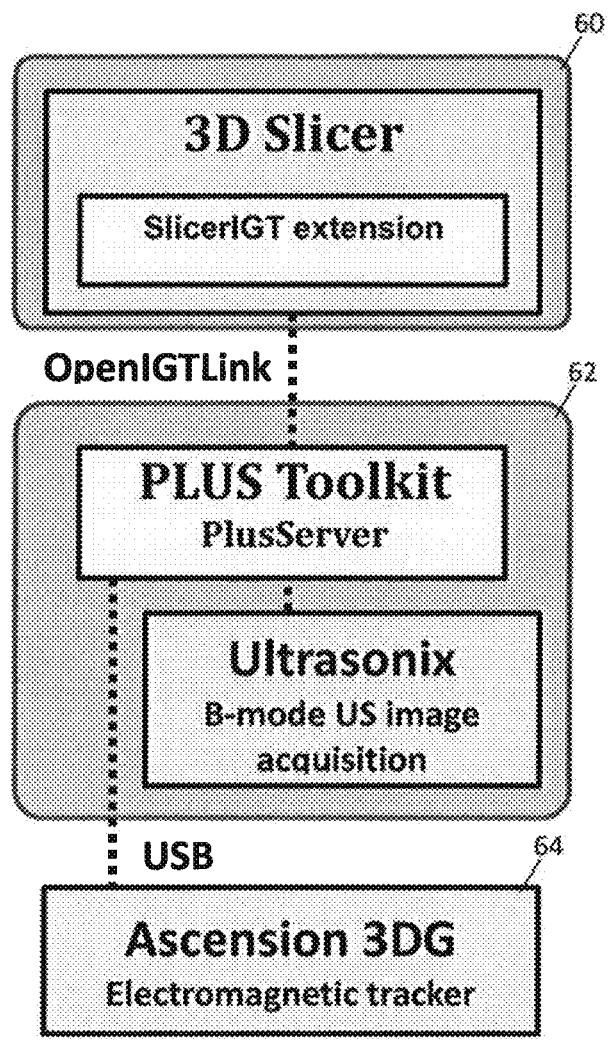
FIG. 7 is a diagram showing more details of the embodiment of FIG. 6.

FIG. 6 is a diagram of an experimental setup. In this embodiment the navigation computer 41 was connected over a network to the US machine 40. The position tracker system 42, reference tracking sensor 46, tracked US transducer 43, and tracked surgical tool 47 were interfaced with the US machine 40. The navigation computer 41 carried out functions as indicated at 56 and 57, interfaced with the tracking hardware 58 and imaging hardware 59. FIG. 7 shows further details of the navigation software components, including SlicerIGT 60, PLUS toolkit 62, and Ascension 3DG (http://www.ascension-tech.com) 64. FIG. 8 is an example of a suitable SlicerIGT configuration file.

The significance of simultaneously achieving adequate surgical margins and cosmesis cannot be overstated; it affects all women undergoing surgical resection for breast cancer, especially breast conserving resection. As confirmed by the below example, the embodiments described herein are expected to significantly reduce the incidence of positive margins during the first attempt at tumor resection in breast-conservation surgery. A decrease in positive margins translates to a direct decrease in patients requiring a second, and sometimes a third surgery to repeat the resection. It also reduces the risk of recurrence and spread of disease. Furthermore, EM navigation has the potential to decrease the amount of healthy tissue removed by improving the precision of the resection, thereby improving cosmetic outcome.

Embodiments described herein allow for rapid intraoperative registration regardless of patient position and compensate for large amounts of motion and deformation of the tissue. The surgeon can use the tracked surgical tool as a "pointer" or "joystick" to manipulate the user interface, without touch, within the sterilized field. Virtual camera orientation can be set up, so that each participating surgeon can have his/her personalised view, showed in the correct viewing angle. Various feedback mechanisms may be implemented to inform the surgeon about proximity of the surgical tool to the tracked tumor margin. For example:

Display screens may be mounted over the surgical field;
The visual feedback may be displayed with integrated Google Glass or similar device for the surgeon;
Visual feedback may be displayed with LED markers, small matrix display, etc., mounted on the surgical too, within the direct view of the surgeon;
Tactile feedback may be provided for the surgeon through the handle of the tool;
Audio warning (beep, bell, horn, etc.) feedback may be generated when margin proximity violation is detected by the tracking system;
Advanced audio feedback may be generated by modulating the frequency components of ambient music or sounds played in the background.

The EM-based navigation technology as described herein may be adapted for a variety of other surgical procedures and minimally invasive interventions; not only in open surgical, but also in laparoscopic and percutaneous settings as well.

It will be appreciated that embodiments described herein may be adapted for use with one or more other spatial tracking technologies, either combined with EM navigation, or instead of EM navigation.

It will be appreciated that, although embodiments have been described and illustrated in detail, various modifications and changes may be made. While several embodiments are described above, some of the features described above may be modified, replaced, or omitted. For example, the method may adapted for use outside the operating room—for cases when it is more important to segment quickly than very accurately. Embodiments may be used not only for surgical interventions, but also for other interventions such as in radiation therapy, e.g., brachytherapy. In a radiation therapy intervention, for example, the surgical tool may be replaced with a radiotherapy tool such as a catheter, a delivery needle, or a device to deliver external beam radiation therapy.

Advantageously, as mentioned above, segmentation may be performed using only one hand. Although segmentation by marking points using 2D ultrasound slices is exemplified, segmentation may be performed using any cross-sectional image, such as, for example, computed tomogaphy (CT), magnetic resonance imaging (MRI), or projection imaging (e.g., X-ray), optionally with visualization such as, for example, maximum/minimum intensity projection or thick slice reformatting.

Tapping a touch-screen, as exemplified above, is a convenient way of interacting with a screen in the operating room, since it does not require a tool (stylus, mouse, etc.) and does not require dragging the finger on a screen (which may be difficult while wearing gloves, may smudge the screen, etc.). However, embodiments work equally well with any pointing device, such as a mouse, stylus, etc.

In one embodiment, creating a 3D shape from a user-defined boundary point set may be performed by a combination of triangulation (e.g., Delaunay triangulation) and smoothing filter (e.g., butterfly subdivision). However, any other surface generation method may be used that ensures the points are enclosed in the surface, the volume enclosed by the surface is minimal, and the surface is smooth.

In one embodiment, all points are defined in a coordinate system established in respect of the tumor or structure. For example, the coordinate system may be established using a sensor that is inserted into the tumor, or using a sensor that is attached to a needle that is fixed into the tumor by hooks, etc. This allows the tumor to arbitrarily move and deform during segmentation. Advantageously, it is not necessary to keep the ultrasound transducer stationary during segmentation: points can be added as desired, i.e., "on the fly". This makes it possible for two clinicians to perform the segmentation—one holding the ultrasound probe, the other marking the points—without one asking the other to move the probe or keep the probe stationary. The clinician marking the points may choose to "freeze" the image at its current location, define the contour on the image, and "unfreeze" the image.

The shape created from imaging may be refined. For example, a refinement may be based on information provided by a 3D tracked margin probe (e.g., if the 3D margin probe indicates that a certain point is inside the tumor, then that point can be included in the tumor shape). As another example, a refinement may be based on information based on a 3D tracked pointing device (e.g., the clinician can touch a point with a 3D tracked stylus to include that point in the shape).

All cited publications are incorporated herein by reference in their entirety.

Embodiments are further described by way of the following examples.

Example 1

For demonstration purposes phantom breast models were created with PVC plastic made to simulate breast tissue density and deformability. As experimental setup based on the embodiment shown in FIG. 6 was used. US-visible tumors were implanted in the breast models. Eight surgical trainees and two staff breast surgeons were recruited to resect a total of 42 synthetic tumors, 21 resections using the wire-localization method alone (control group), and 21 using the wire-localization-EM-augmented method (EM navigation group). Participants resected an equal number of tumors using each method. Both groups were instructed to raise a mock skin flap and to resect down to 'chest wall' as per standard of practice. For the control method, participants were instructed to use the standard procedure for wire-localization resection. For the EM navigation method, participants were given instructions on how to utilize the navigation system to visualize their surgical instrument in relation to the resection volume. The resected volumes were analyzed for presence of tumor at the edge of the resection in all six planes, and size and weight of resected volume in relation to breast model. Participants were asked to give feedback on the ease of using EM navigation in the surgical procedure.

The positive margin rate in the control group was 42.9% (9 of 21), and the positive margin rate in the EM navigation group was 19.0% (4 of 21). The data revealed a trend toward reducing positive margins ($p=0.18$). There was no difference between the two groups in the relative size of the resected volume ($p=0.87$). Feedback from the participants stated that none of the participants found that the EM sensors interfered with the surgical procedure, and that the EM navigation was somewhat easy to use. The average amount of tissue resected in the EM group was 37.7 g (SD=9.8 g) and in the control group was 36.3 g (SD=14.5 g), indicating statistically equivalent tissue sparing.

Subsequently, two simulated tumor excision surgeries were successfully performed on human cadavers, showing feasibility of navigation under realistic conditions. The system has been used in clinical testing for safety and feasibility. Five breast excision surgeries have been completed. Setup and calibration of the navigation system takes 5 to 10 minutes, and requires one dedicated personnel operating the navigation computer. Positive feedback on the navigation system was received from surgeons though a survey completed after each operation. No breach of sterility or other issues have been detected with the safety and feasibility of the navigation system. In all patient cases the tumor excision was complete and the margins were negative.

Example 2

This example demonstrates catheter targeting under electromagnetic guidance in breast brachytherapy. Breast cancer is commonly treated with lumpectomy followed by radiation therapy. Accelerated partial breast irradiation (APBI) with high dose rate (HDR) brachytherapy by means of interstitial catheters is a treatment option. Hollow needles are inserted into the breast and then a flexible catheter is passed through each needle. The needles are removed, leaving the catheters in the breast. The catheters need to be positioned in and around the tumour bed with even spacing. Needles can be inserted freehand or using a template. This procedure presents a challenge firstly in localizing the tumour bed and secondly because the breast is a mobile and deformable organ which cannot be adequately immobilized. Fluoroscopy or ultrasound are used to localize the tumour bed, but the lack of reliable spatial relationship between reference points on the skin and the tumour bed makes it difficult to maintain a precise sense of the catheter paths and trajectories relative to the tumour bed.

Figure 12A:
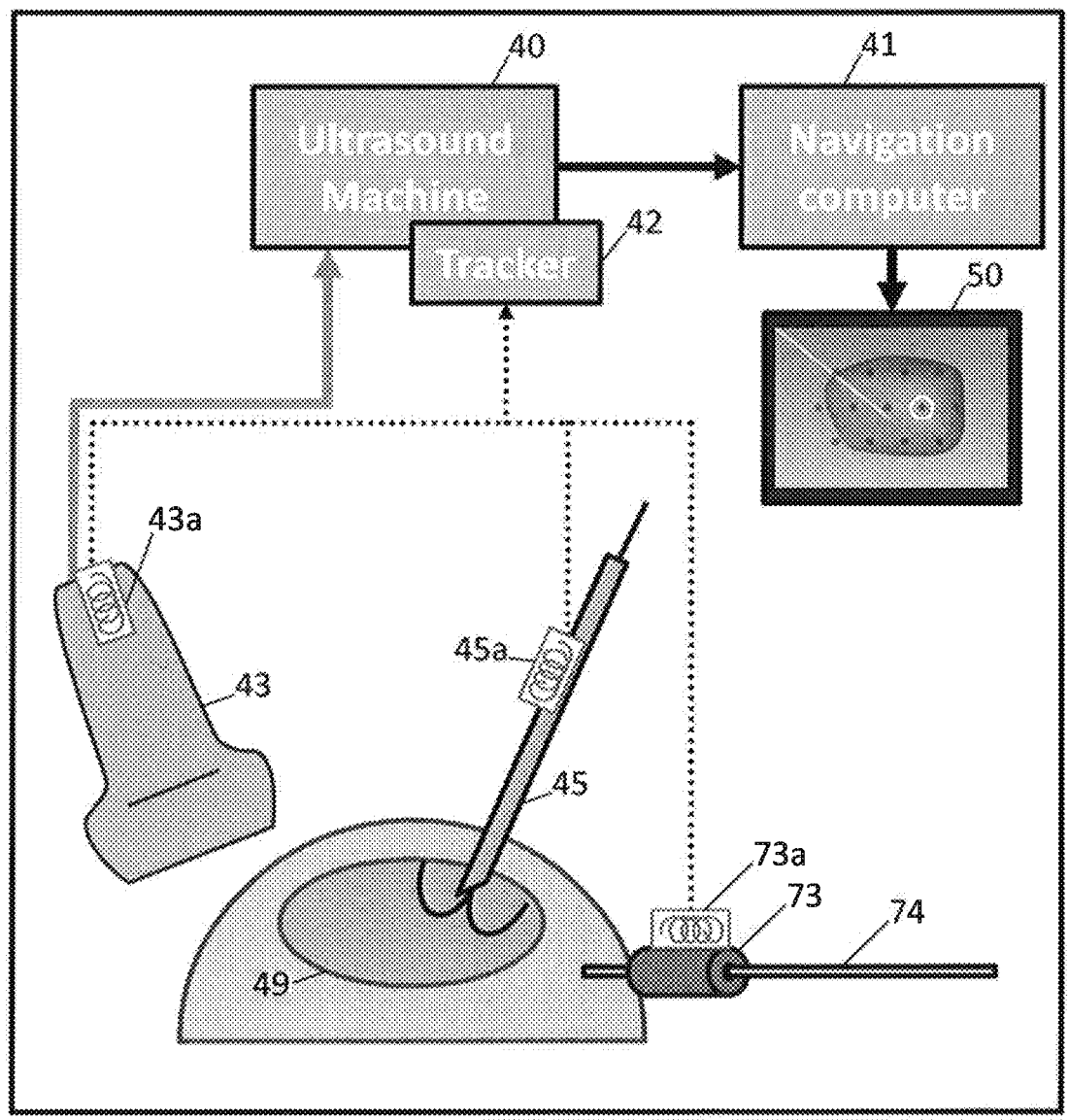
FIGS. 12A and 12B are diagrams showing catheter targeting under EM navigation in breast tumor brachytherapy, according to one embodiment.
Figure 12B:
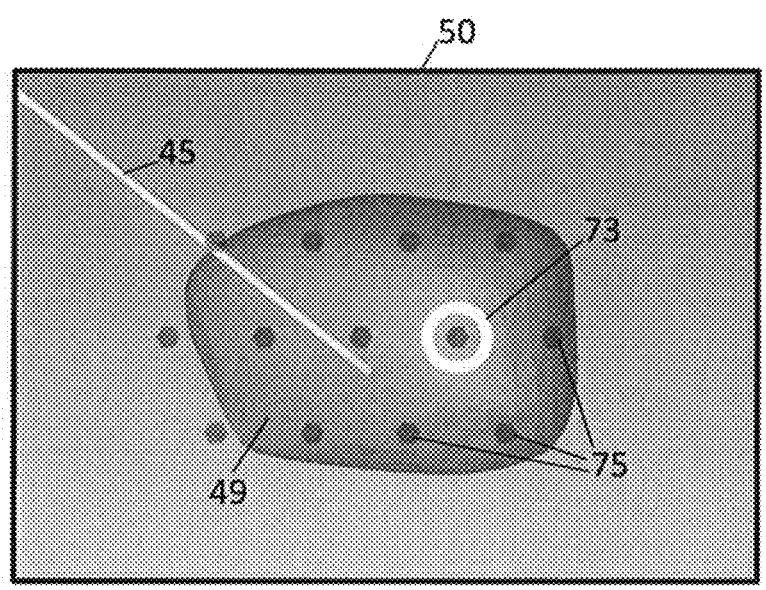

To ensure accurate catheter placement and optimal spacing, electromagnetic (EM) guidance as described herein may be employed (FIG. 12A). In this example an EM-tracked localization needle 45 was inserted into the tumour bed under ultrasound guidance, and a hook was deployed to anchor the needle in place. This established a coordinate system locally-rigid to the tumour bed. The tumour bed was segmented in this coordinate system using tracked ultrasound, which created a tracked model of the tumour bed in a virtual 3D view 50 (or simply "view", shown in detail in FIG. 12B).

The radiation oncologist pointed a tracked needle guide 73, 73a (or simply "guide") toward the tumour bed 49 with the help of the view 50. When the guide was pointed at the tumour bed, a catheter needle 74 was inserted though the tissue. After the first catheter needle insertion, all planned catheter paths 75 were drawn on the view 50 to facilitate evenly-spaced, parallel catheter insertions. The guide was aligned with a planned catheter path for each subsequent insertion.

The apparatus included software built on the 3D Slicer (www.slicer.org) and PLUS (www.plustoolkit.org) platforms, as described above. Ultrasound image and tracking data were collected by PLUS running on an Ultrasonix SonixTouch with GPS extension (Ultrasonix, Richmond, BC, Canada) and relayed to 3D Slicer running on a navigation computer. A tracked L14-5 linear probe (Analogic, Peabody, Mass., USA) and several Ascension TrakStar model 800 sensors (Northern Digital, Waterloo, Ontario, Canada) were used for collecting image and tracking data. The image and tracking data were manipulated in 3D Slicer using a series of configurable and reusable modules within 3D Slicer.

A radiation oncology resident performed catheter needle insertions on opaque breast phantoms made with soft plastic (M-F Manufacturing, Fort Worth, Tex., USA), The phantoms had CT- and ultrasound-visible tumour beds within them. The goal for each phantom was to insert a row of four catheters through the tumour bed, with 1 cm spacing between catheters. Catheter insertions were carried out under ultrasound guidance only for two phantoms, and under EM and ultrasound guidance (as described above) for two phantoms. CT scans of the phantoms were acquired after the insertions to verify the positions of the catheters with respect to their target tumour bed.

Under ultrasound guidance only, seven of eight catheters completely passed through the tumour bed. Under EM and ultrasound guidance, all eight catheters passed through the tumour bed. We did not observe improvement, in maintaining even spacing between catheters in this study. Using EM guidance, the first inserted catheter went exactly where it was intended to go by the resident. This insertion is particularly important because the other catheters are positioned relative to it. These results suggest that the guidance system helped the resident to precisely target the desired point on the tumour bed without any other real-time information or feedback.

EM guidance also offers other opportunities in HDR brachytherapy. Segmentation of the catheter paths on the planning CT need not be done manually but may be recorded by a small sensor as it is fed through each catheter. The catheter needle path may also be tracked in real time using EM tracking.

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

The invention claimed is:

1. A surgical navigation method, comprising:
disposing one or more electromagnetic (EM) tracked localization devices in a tissue volume;
generating images of the tissue volume in real time using an EM tracked imaging device, wherein the images of the tissue volume are only generated intraoperatively;
using only data points in the images of the tissue volume to intraoperatively delineate a portion of the tissue volume at its current location;
disposing an EM tracked surgical tool in the tissue volume;
using EM tracking of the one or more localization devices, the imaging device, and the surgical tool to three-dimensionally visualize and register the surgical tool relative to the intraoperatively delineated portion of the tissue volume in real time; and
providing feedback about the location of the surgical tool relative to the intraoperatively delineated portion of the tissue volume.

2. The method of claim 1, wherein EM tracking comprises:
creating a global frame of reference for EM tracking;
using at least one EM sensor attached to the tissue to track local deformation and movement of the tissue volume; and
using an EM sensor to track movement of the surgical tool.

3. The method of claim 2, wherein creating the global frame of reference for EM tracking comprises using an EM sensor attached to the patient.

4. The method of claim 2, wherein using at least one EM sensor to track local deformation and movement of the tissue volume comprises using an EM sensor attached to each of one or more wire-localization needles.

5. The method of claim 1, comprising displaying and dynamically updating the three-dimensional delineation of the portion of the tissue volume as data points from the images are added or removed.

6. The method of claim 1, wherein providing feedback comprises one or more of visual, tactile, and auditory feedback.

7. The method of claim 1, applied to a tissue resection procedure.

8. The method of claim 1, wherein the tissue volume comprises a tumor.

9. The method of claim 7, wherein the resection procedure is a lumpectomy in breast tissue.

10. The method of claim 1, applied to a brachytherapy procedure.

11. The method of claim 1, wherein the surgical tool comprises a catheter, needle, cutting tool, cautery tool, or radiation therapy device.

12. Apparatus for surgical navigation, comprising:
an electromagnetic (EM) device that creates a reference frame for EM tracking in three dimensions;
one or more localization devices adapted to be attached to tissue and to provide EM tracking of local deformation and movement of a tissue volume;
an EM sensor adapted to be attached to a surgical tool;
a processor that receives images of the tissue volume in real time from an EM tracked imaging device, wherein the images of the tissue volume are only generated intraoperatively, EM tracking data of the one or more localization devices, and EM tracking data of the surgical tool, intraoperatively generates a three-dimensional delineation of a portion of the tissue volume using only data points in the images of the tissue volume, and three-dimensionally registers the intraoperatively delineated portion of the tissue volume with the surgical tool in real time; and
an output device.

13. The apparatus of claim 12, wherein the output device provides feedback about the location of the surgical tool relative to the tissue volume.

14. The apparatus of claim 12, wherein the EM device that creates a reference frame comprises an EM sensor attached to the patient.

15. The apparatus of claim 12, wherein the one or more localization devices adapted to be attached to the tissue comprise at least one wire-localization needle.

16. The apparatus of claim 12, wherein the tissue volume comprises a tumor.

17. The apparatus of claim 12, wherein the tissue comprises breast tissue.

18. The apparatus of claim 13, wherein the feedback comprises one or more of visual, tactile, and auditory feedback.

19. The apparatus of claim 12, wherein the surgical tool comprises a cutting tool, cautery tool, catheter, needle, or radiation therapy device.

20. Programmed media for use with a processor, comprising:
code stored on non-transitory storage media compatible with the processor, the code containing instructions to direct the processor to:
receive images of a tissue volume in real time from an EM tracked imaging device, wherein the images of the tissue volume are only generated intraoperatively, and intraoperatively generate a three-dimensional delineation of a portion of the tissue volume using only data points in the images of the tissue volume;
receive EM tracking data of one or more EM-tracked localization devices and of an EM-tracked surgical tool, and use the EM tracking data to three-dimensionally register the intraoperatively delineated portion of the tissue volume with the EM-tracked surgical tool in real time; and
produce an output comprising feedback about the location of the EM-tracked surgical tool relative to the intraoperatively delineated portion of the tissue volume in real time.

21. The programmed media of claim 20, wherein the output comprises images of the EM-tracked surgical tool registered in the intraoperatively delineated portion of the tissue volume in real time.

* * * * *